United States Patent [19]
Heinonen

[11] Patent Number: 6,032,667
[45] Date of Patent: Mar. 7, 2000

[54] VARIABLE ORIFICE PULSE VALVE

[75] Inventor: Erkki Heinonen, Helsinki, Finland

[73] Assignee: Instrumentarium Corporation, Helsinki, Finland

[21] Appl. No.: 08/961,338

[22] Filed: Oct. 30, 1997

[51] Int. Cl.[7] .................................................. A61M 16/00
[52] U.S. Cl. .............................. 128/205.24; 128/207.12; 128/204.19; 128/204.21; 128/203.12
[58] Field of Search .................. 128/205.24, 204.19, 128/204.21, 204.23, 203.12, 207.12, 204.18, 200.24

[56] References Cited

U.S. PATENT DOCUMENTS

| | | | |
|---|---|---|---|
| 4,401,116 | 8/1983 | Fry et al. | 128/205.24 |
| 5,411,059 | 5/1995 | Sever et al. | 128/205.24 |
| 5,531,218 | 7/1996 | Krebs | 128/203.12 |
| 5,558,083 | 9/1996 | Bathe et al. | 128/203.12 |
| 5,771,884 | 6/1998 | Yarnall et al. | 128/204.19 |
| 5,791,339 | 8/1998 | Winter | 128/205.24 |
| 5,839,433 | 11/1998 | Higenbottam | 128/204.21 |
| 5,862,802 | 1/1999 | Bird | 128/204.21 |

FOREIGN PATENT DOCUMENTS

| | | | |
|---|---|---|---|
| 589751 | 3/1994 | European Pat. Off. | |
| 640356 | 3/1995 | European Pat. Off. | |
| 640357 | 3/1995 | European Pat. Off. | A61M 16/12 |
| 659445 | 6/1995 | European Pat. Off. | A61M 16/00 |
| 783896 | 7/1997 | European Pat. Off. | |
| 806216 | 11/1997 | European Pat. Off. | |
| WO 95/10315 | 4/1995 | WIPO | A61M 16/00 |

*Primary Examiner*—John G. Weiss
*Assistant Examiner*—Virendra Srivastara
*Attorney, Agent, or Firm*—Andrus, Sceales, Starke & Sawall

[57] ABSTRACT

A variable orifice pulse valve has a small internal volume for providing small, accurately measured pulse volumes of gas. The valve may be employed to supply a very small quantity of a therapeutic gas or a diagnostic gas into the breathing gases of a patient. The valve has a housing with an inlet for receiving the gas and an outlet providing the pulsatile discharge of the gas. A chamber, formed in the housing, has a first opening in fluid communication with the inlet and a second opening in fluid communication with the outlet. The intermediate chamber is formed to have a small volume compared to the minimum pulsatile gas discharge volume of the valve. A spring biases a variable orifice member toward the first opening and a solenoid moves the variable orifice member away from the first opening to form an orifice that meters a dose of gas into the valve. A sealing member is spring biased into sealing engagement with the second opening. A second control solenoid operates to move the second sealing member out of engagement with the second opening to form a pulse orifice in the valve that provides the pulsatile discharge of gas from the outlet. An outlet chamber of the valve may include a further inlet providing a carrier gas that sweeps the gas pulse exiting from the intermediate chamber out of the valve to prevent the gas pulse from being trapped in the valve.

35 Claims, 3 Drawing Sheets

VARIABLE ORIFICE PULSE VALVE

BACKGROUND OF THE INVENTION

The present invention relates to a unitary, variable orifice pulse valve, for providing small pulsed volumes of gas. The valve may be used to supply a small dose of therapeutic gas, such as NO, or diagnostic gas, such as $SF_6$, into the breathing circuit for a patient. The valve has a reduced internal volume to achieve accurate measurement of pulse volume. The present invention also relates to a special gas dose delivery unit and respiration equipment incorporating such a valve.

U.S. patent application Ser. No. 08/841,466 filed Apr. 22, 1997 by the present applicant describes an apparatus and method for the pulsatile dosing of a specified, special gas into a patient airway. The dose volume is defined by the dose pulse length and the flow occurring during the pulse. The volumes to be delivered may range from 10 $\mu l$ up to 20 ml. The pulse lengths may vary from 100 ms up to 1 s, and the flows from 0.05 ml/s to 20 ml/s. Proportionally adjustable valves can accommodate this flow range.

A problem with these valves is, however, in their dynamic behavior. They may not be sufficiently rapid, particularly when considering the smallest flows, where the fastest response is needed. Thus the system may have difficulties in dosing gas pulses of the smallest volumes.

In current state of the art, the dynamic range problem has been dealt with by diluting the special gas to enlarge the actual dose volumes to be delivered. European patent document EP 659,445 discloses a nitric oxide (NO) delivery system where this dilution can be done on "on fly" when the "system is otherwise unable to reduce the concentration to the desired point." The technique employs an additional diluting gas (nitrogen) source and a diluted NO concentration sensor for controlling the dilution. The disadvantages of this system are the increased complexity, size, weight, and cost caused by the diluting apparatus and instrumentation. Alternatively, the dilution may take place by selecting a tank of an appropriate concentration for the current need. A range of tank concentrations are presented, e.g. in U.S. Pat. No. 5,531,218 and European patent document EP 640,357. If the concentration in the tank is inappropriate for the treatment of the patient, it may be necessary to change tanks. Cumbersome maneuvers may be required when a need to change the concentration arises during the treatment of the patient.

A technique for creating small pulses is presented in patent document WO 95/10315. The delivery system shown in the document has a constant 12 l/min flow source and an on/off switch valve to create pulses. This kind of construction is cost-effective and simple. The low limit for the doses is set by the valve control time resolution. The system can provide pulses with a minimum length of 5 ms, corresponding to 1 ml of volume. However, even this volume is large compared to portions of the specified pulse volume range noted above. Furthermore, user control over the pulse amplitude and length are lost when pulse length is employed for dose control and the flow rate is fixed. Pulse width control is needed when a need to spread out the dose over a definite period of inspiration exists. The flow control may be beneficial in adjusting the local effectiveness of the treatment.

For safety reasons, a special gas dose delivery system should have two redundant means to prevent unintentional dosing of the patient. The apparatus described in applicant's earlier application and in European patent document EP 659,445 use a proportionally adjustable solenoid valve for the flow regulation, whereas U.S. Pat. No. 5,561,218 shows a control valve which could also be a proportional valve, but the disclosure of the patent does not have a detailed description. All of these systems do have the safety redundancy in the form of an on-off type solenoid valve in addition to the proportional valve. A fast response time is characteristic of an on-off solenoid valve.

The proportional adjustability of the proportional valve and the fast dynamic behavior of an on-off valve suggest the use of the proportional valve as a variable orifice and the on-off valve for delivery of the doses of gas.

However, a problem in such an arrangement comes from the volume existing between the proportional valve and the on-off valve. This volume comprises the internal volume of the valves and the intermediate channel volume between the valves. Due to the construction of such valves, the intermediate channel volume is not likely to be less than 20 $\mu l$. The internal volumes of the valves depend on the valve type, but for commercially available miniature valves, it starts from about 40 $\mu l$. These volumes, which together comprise easily 100 $\mu l$, represent a pressure chamber for an uncontrollable dose of gas. The quantity of such a dose is dependent on the pressure chamber volume and the chamber pressure. As a result of the foregoing, the dose volume becomes uncontrollable when using the proportional valve as a variable orifice and the on-off valve for delivery of the doses.

The flow measurement of the dose has to be carried out upstream of the on-off valve to avoid the pumping effect on the flow measurement caused by the variable pressure conditions in the breathing circuit. The proportional valve acts as a flow restrictor. The more it restricts the flow the less the volume of the pulse. Downstream of the proportional valve are the uncontrollable dose volume and the on-off valve. Upon opening of the on-off valve, the pressure existing in the intermediate channel volume discharges and the pressure rapidly equilibrates with the pressure downstream of the on-off valve, which is practically near ambient pressure. After closing the on-off valve, the intermediate chamber will be reloaded with gas and re-subjected to the pressure of the gas. This re-application of the pressure takes place slowly through the orifice of the proportional valve. The reload volume can be detected and measured by the dose flow sensors, but only after the dosing has taken place.

At sea level ambient pressure, the upstream pressure of the delivery system is preferably 90 kPa overpressure or more, e.g. 150 kPa, to guarantee sonic flow in the discharge orifice when the valve opens for gas flow. The advantage of such a flow is the elimination of the effect of the variable pressure condition in the breathing circuit on the dose flow. With 100 kPa overpressure in the 100 $\mu l$ pressure chamber formed in the valves and intermediate channel, the uncontrollable dose will become 100 $\mu l$ by volume. This represents a volume tenfold greater than the minimum dose requirement noted, but could be even more depending on the valves used, and represents the minimum dose volume that can be delivered with such an arrangement.

Inverting the order of the proportional and on-off valves, to place the on-off valve upstream of the proportional valve would help in regulating the dose volume. However, the dose timing would be totally lost, the dose pulse "leaking" little by little through the orifice of the proportional valve over a relatively long time period.

BRIEF SUMMARY OF THE INVENTION

The object of the present invention is to overcome the problem heretofore caused by the intermediate chamber volume existing between the separate proportional and dosing valves by providing a unitary, variable orifice, pulse valve combining the different characteristics previously provided by the two separate valves. When operating the valve of the present invention, a variable orifice is used to adjust the flow through the valve. The variable orifice is adjusted by a proportional solenoid to match the flow with the required dose volume to be delivered. This orifice may be adjusted on a pulse to pulse basis or even within the pulses. Advantageously the valve is not closed between the pulses, thereby to avoid the need for large and, hence, slow changes. A pulse valve is used to enable and disable the flow through the variable orifice to match the needs of the pulsatile delivery.

In the valve of the present invention, the intermediate volume between the variable orifice and the pulse valve orifice can be easily reduced down to 2 μl and the internal volume of the valve minimized. Thus, with 100 kPa overpressure, the uncontrollable dose of gas will be 2 μl, complying with the minimum anticipated dose in a highly satisfactory manner.

Very small dose pulse volumes may be trapped in the internal volume of the outlet portions of the valve. To eliminate this, it is advantageous also to minimize the volume of these portions. To this end, a carrier gas for the special gas doses may be conducted through the outlet portion of the valve and out the valve discharge to flush the special gas doses out of the valve.

The present invention is also directed to providing a special gas dose delivery unit and respiration equipment incorporating such a valve.

BRIEF DESCRIPTION OF THE SEVERAL VIEWS OF THE DRAWING

The invention will be further understood by reference to following detailed description taken in conjunction with the drawing in which.

DETAILED DESCRIPTION OF THE INVENTION

Figure 1:
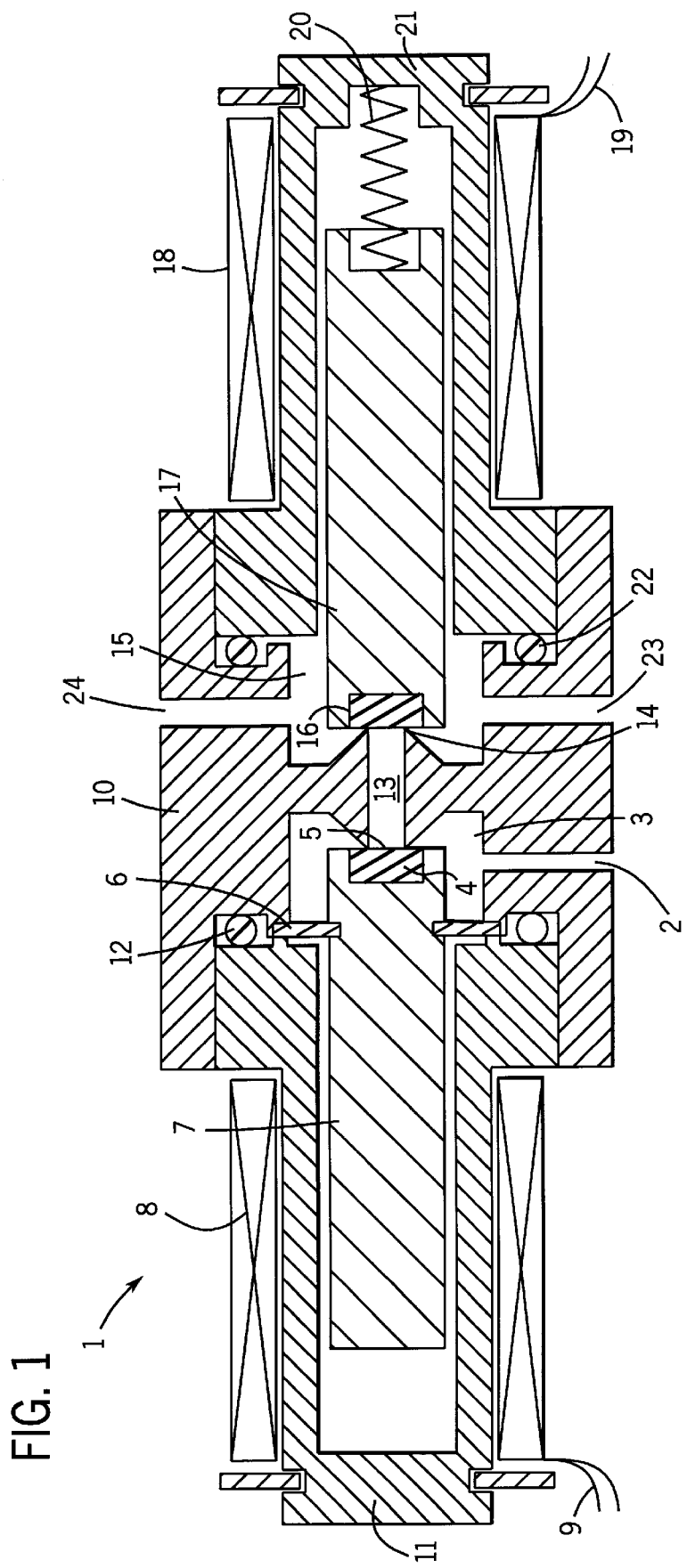
FIG. 1 is a cross sectional view of a variable orifice pulse valve of the present invention.

FIG. 1 shows the structural elements of the variable orifice pulse valve 1 of the present invention in cross section. The special gas to be dosed is supplied in the inlet connector opening 2 of variable orifice pulse valve body 10. This opening leads to the variable orifice chamber 3 where a variable orifice member 4 and the orifice 5 are located. The variable orifice chamber 3 is defined by the variable orifice pulse valve body 10 and the variable orifice housing 11. Seal 12 is provided between body 10 and housing 11. The variable orifice member 4 is located at the end of a ferromagnetic stem member 7 located in variable orifice housing 11. Variable orifice member 4 may incorporate a resilient seal for coacting with orifice 5, if desired. Ferromagnetic stem member 7 will be located in the magnetic field produced by solenoid coil 8 when supply cables 9 are connected to a source of electrical current. Variable orifice pulse valve 1 also includes a spring 6, shown in annular plate form in FIG. 1, surrounding and secured to stem member 7, and retained between body 10 and housing 11. Spring 6 could as well be of another suitable type.

An electrical current in solenoid coil 8 creates, through the resulting magnetic field, an opening force on the stem member 7 and variable orifice member 4 tending to move stem member 7 to the left in FIG. 1. This opening force acts against the force of spring 6. The larger the current in solenoid coil 8, the larger the force, and the larger the opening between the member 4 and the orifice 5 so as to vary the size of the orifice.

Figure 2:
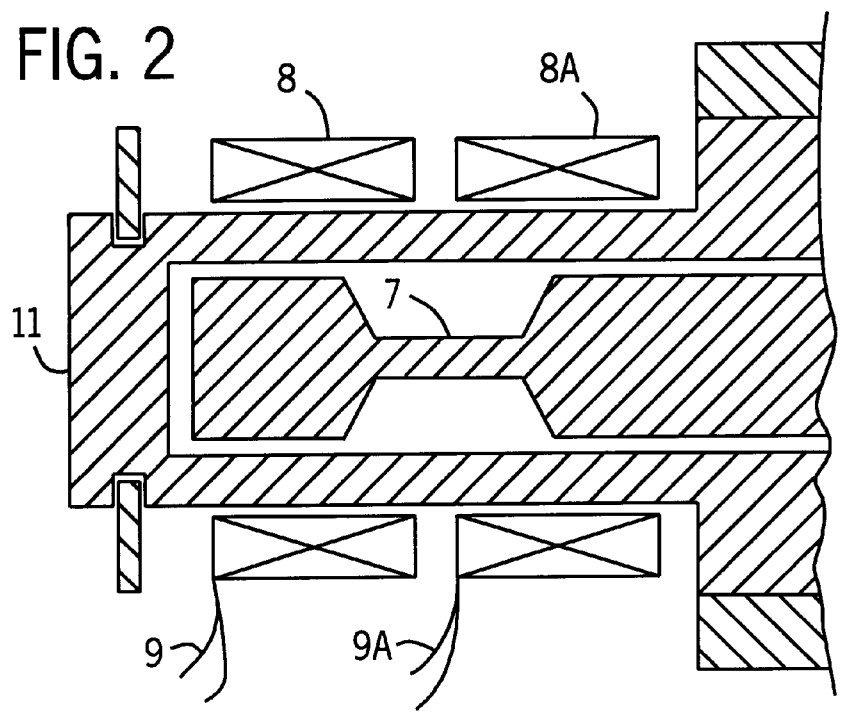
FIG. 2 is a cross sectional view of a modification of the variable orifice pulse valve of the invention.

While FIG. 1 shows use of solenoid coil 8 and spring 6 to control the movement of stem member 7, as shown in FIG. 2, it is also possible to use two, opposing solenoids 8, 8A connected to supply cables 9, 9A, if desired, with suitable modification of stem member 7.

The gas flows through the variable orifice 5 to the intermediate chamber 13 formed in valve body 10. The volume of intermediate chamber 13 is minimized in the invention to a level which is negligible or small with respect to the volumes involved in the application to which the valve is put. Depending on the quantities involved in the application to which the valve is put, the volume of intermediate chamber 13 may be less than 50 μl, less than 20 μl, less than 10 μl, or less than 5 μl. From the intermediate chamber 13, the flow path continues through the pulse valve orifice 14 into outlet chamber 15. The opening and closure of the pulse valve orifice 15 is controlled by a pulse valve member 16 at the end of a ferromagnetic stem member 17. Pulse valve member 16 preferably has a seal formed of resilient material for coacting with orifice 14. Ferromagnetic stem member 17 is moveable within pulse valve housing 21 under the effects of an opening force caused by the magnetic field created by solenoid 18 when electrical current is applied to the solenoid through supply cables 19 and a closing force caused by pulse spring 20. Pulse spring 20 may be a coil spring acting on the end of stem member 17 opposite pulse valve member 16. The outlet chamber 15 is enclosed between valve body 10 and pulse valve housing 21 which is sealed with the body by seal 22. The outlet chamber 15 has an outlet connector opening 23. This opening is the end point of the variable orifice pulse valve flow path that commences with the inlet connector opening 2.

The movement of stem member 17 may be controlled by two solenoids in the manner shown in FIG. 2, if desired.

To optimize the construction of variable orifice pulse valve 1 for minimal volume of intermediate chamber space 13, it is advantageous to make the intermediate chamber in the form of a straight channel having the variable orifice 5 at one end and the pulse valve orifice 14 at the other end. This suggests the positioning of the stem members 7, 17 and the solenoids 8, 18 in the aligned manner presented in FIG. 1.

Figure 3:
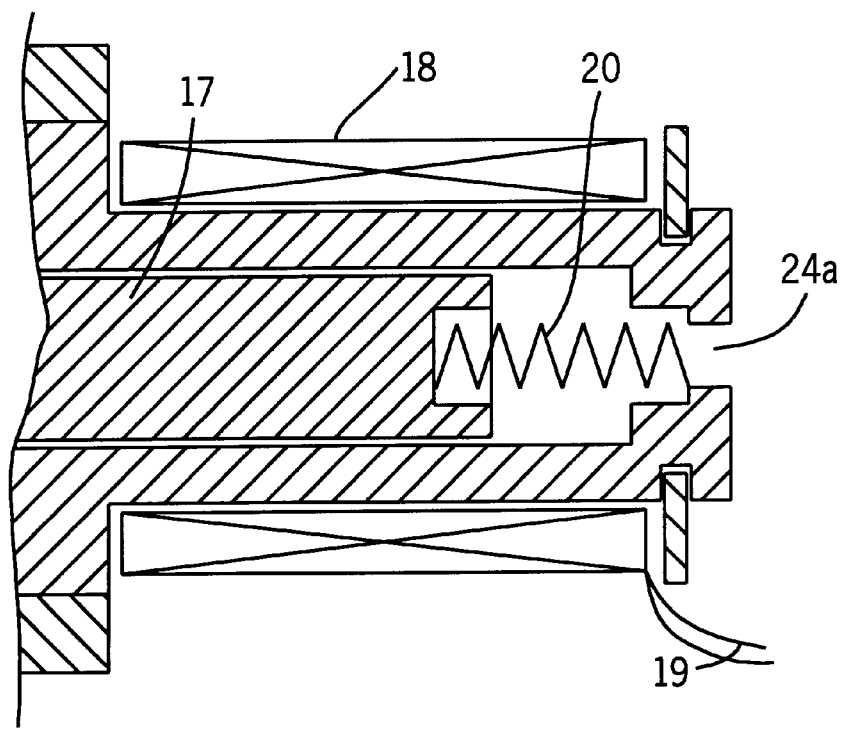
FIG. 3 is a cross sectional view of a further modification of the variable orifice pulse valve of the invention.

The valve 1 shown in FIG. 1 also has optionally another connector opening, flush flow inlet connector opening 24, leading to outlet chamber 15. As hereinafter described in detail, this inlet connector opening supplies a carrier gas for the pulse doses that enhances the washout of the pulse doses from the valve into the discharge from the valve. The volume of the outlet chamber 15 may be as much as 100 μl. Thus very small pulse doses are easily trapped in this volume and the accuracy of dose measurement will be lost. A supply of carrier gas avoids this problem. Alternatively, the flush flow inlet connector opening may be located at the end of pulse valve housing 21 as shown in FIG. 3 by the numeral 24a. This positioning will further enhance the washout when the carrier gas flow sweeps throughout outlet chamber 15.

Figure 4:
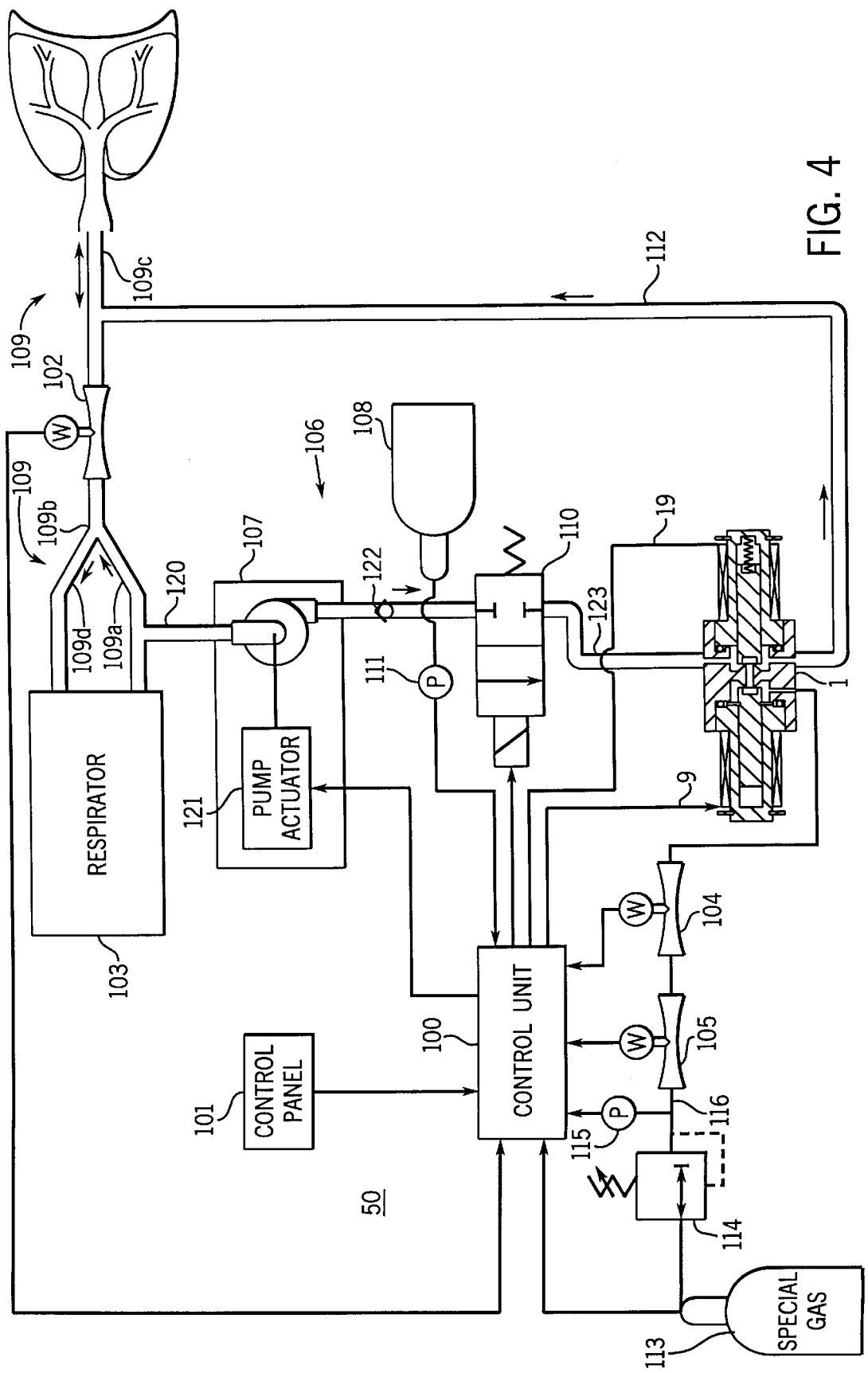
FIG. 4 is a schematic diagram showing a special gas dose delivery unit and patient respiration equipment incorporating a variable orifice pulse valve.

FIG. 4 shows a special gas dose delivery unit 50 and respiration equipment incorporating the above described variable orifice pulse valve 1. The respiration equipment includes respirator 103 used to ventilate the lungs of a patient. Variable orifice pulse valve 1 may be used to supply, or "dose", a special gas into the breathing gases provided to the patient by the respirator 103. A typical special gas is nitric oxide (NO), used for improving lung perfusion and thus patient $O_2$ uptake thereby raising blood oxygen saturation. Other special gases that may be used are $SF_6$ (sulphur hexa-fluoride) for measuring the lung functional residual volume (FRC) and nitrous oxide ($N_2O$) for measuring lung capillary blood flow.

Respirator 103 is connected to a breathing circuit 109 of the respiration equipment comprising an inspiratory limb 109a, a Y-piece connector 109b, a patient limb 109c, and an expiratory limb 109d. A flow measuring element 102 may be connected in patient limb 109c. The construction and operation of the respirator shown in FIG. 4 is more fully described in applicant's earlier patent application Ser. No. 08/841,466, noted above.

FIG. 4 shows the special gas dosing unit 50 separated from respirator 103, but the two elements could be integrated together, if desired. The special gas dosing unit 50 includes a high pressure special gas source 113 connected to pressure regulator 114. Pressure sensor 115 monitors the output pressure of pressure regulator 114 in conduit 116. Redundant flow sensors 104 and 105 measure the flow in special gas supply conduit 116. Special gas supply conduit 116 is connected to inlet connector opening 2 of variable orifice pulse valve 1.

Control unit 100 of the special gas dosing unit 50 is connected with the breathing gas flow sensor 102 connected in patient limb 109c. Control unit 100 is also connected to control panel 101 which provides dose related parameters to control unit 100. The dose parameters may comprise, for example, dose volume, pulse length, dose flow, inhaled gas concentration, triggering information, and the type of special gas to be dosed. Control unit 100 also receives inputs from pressure sensor 115, flow sensors 104 and 105, and a special gas source identification signal line from special gas source 113. Control unit 100 provides output signals to solenoid coils 8, 18 of variable orifice pulse valve 1 in supply cables 9 and 19, respectively.

Outlet connector opening 23 of variable orifice pulse valve 1 is connected to special gas dosing line 112 which is connected in the patient limb 109c of breathing circuit 109.

In operation, control unit 100 provides a signal to start the dose which will activate the variable orifice elements 4, 5, 7, and 8 of valve 1 to a preferably precalibrated initial value and activate the pulse valve elements 14, 16–18. The variable orifice 5 is made small, compared to the pulse valve orifice 14, so that gas in the intermediate chamber 13 will be discharged by the overpressure existing in the chamber. This discharge is not sensed by the dose monitoring means 104 and 105. Thereafter during the dosing time, control unit 100 monitors the dosing to dosing line 112, as by comparing information from sensors 104, 105 with reference dose information. The control unit stops the pulse at a time derived from the reference and monitored information by closing pulse valve 1 at pulse valve orifice 14. The pulses of gas will be supplied to special gas dosing line 112 for delivery to patient limb 109c.

It is preferable that variable orifice 5 is not completely closed so that the intermediate chamber 13 will reload slowly with gas through the variable orifice 5 to the supply pressure. The quantity of gas used to reload space 13 is sensed by sensors 104, 105. Thus the initial volume of gas discharged from the intermediate chamber 13 can be taken into consideration when adjusting the variable orifice for the next dose of special gas. Therefore, uncontrollability in the dose can be totally eliminated, as long as the amount of the dose is larger than the discharge volume of intermediate chamber 13 of variable orifice pulse valve 1. In a typical embodiment, this would be a dose larger than 3 $\mu$l. Particularly when dosing tiny pulses of special gas, the variable orifice 5 is not closed but advantageously only modified for the next dose according to the reference and monitored information obtained from the previous dose. This is because closing the variable orifice between the pulses does not achieve the benefit of the high speed dosing. With large pulses of special gas, closure of variable orifice 5 may take place e.g. for purposes of power consumption optimization. The limit between large and tiny pulses depends largely on the overall dimensioning and configuration of the variable orifice 5, but as an example it could be 10% of the maximum dynamic capacity of the variable orifice.

The advantageousness of positioning the variable orifice 5 upstream of pulse valve orifice 14 becomes apparent from FIG. 1. If the order of the orifices in the flow stream was reversed, the variable orifice 5 would remain open between the doses. The intermediate chamber 13, which is reloaded with gas during the period of the gas pulse would discharge slowly between the pulses, so that the timing accuracy would be lost. However, it is possible to employ variable orifice pulse valve 1 in the reversed flow stream manner, if desired.

The use of the valve of the present invention provides the features noted above while at the same time providing redundant means for preventing unintentional dosing of the patient as a result of the presence of the two orifices in the valve.

FIG. 4 also shows source 106 for a carrier gas which receives the special gas dose and carries it through dosing line 112 to the patient. Source 106 withdraws respiratory gases from the inspiration limb 109a of the breathing circuit 109 through conduit 120. Carrier gas source 106 includes pump 107 controlled by pump actuator 121. Check valve 122 is provided in the output of pump 107.

Pump 107 pressurizes tank 108 with gas obtained from inspiratory limb 109a of breathing circuit 109. The tank pressure is monitored to an appropriate level by pressure sensor 111. Tank 108 is connected through flush valve 110 to inlet connector opening 24, 24a of valve 1 by conduit 123.

To obtain carrier gas flow, control unit 100 actuates flush valve 110. The supply of carrier gas from carrier gas source 106 through conduit 123 to variable orifice pulse valve 1 and dosing line 112 flushes the special gas dose from outlet chamber 15 and provides a high speed flow that advances the dose in dosing line 112 rapidly to the dosing point in patient limb 109c of breathing circuit 109. The operation of flush valve 110 may be synchronized in a desired manner with the operation of variable orifice pulse valve 1.

Positioning pulse valve orifice 14 down stream of variable orifice 4 insures that the flush flow does not enter the intermediate chamber 13, which might cause, e.g. contamination problems, depending on the application to which the valve is put.

I claim:

1. A unitary, variable orifice pulse valve comprising:
   a housing having an inlet for receiving gas and an outlet discharging gas from the valve;

a chamber formed in said housing intermediate the inlet and outlet of said housing, said intermediate chamber having a first opening in fluid communication with one of said inlet and outlet and a second opening in fluid communication with the other of said outlet and inlet;

variable orifice forming means in said housing relatively movable with respect said first opening of said chamber;

first operating means operatively associated with said variable orifice forming means, said first operating means moving said variable orifice forming means with respect to said first opening responsive to a variable magnitude signal applied to said first operating means to cause said variable orifice forming means to form a variably sized orifice at said first opening for metering a quantity of gas, the size of said orifice being proportional to the magnitude of the signal;

sealing means in said housing relatively movable with respect to said second opening of said chamber for sealing and unsealing said second opening;

means for urging said sealing means into sealing engagement with said second opening to block fluid communication through said second opening; and second operating means operatively associated with said sealing means, said second operating means being responsive to a signal applied thereto to move said sealing means out of engagement with said second opening for a period of time to provide a discharge of gas from said valve.

2. A variable orifice pulse valve according to claim 1 wherein said intermediate chamber comprises a generally straight flow channel between said first and second openings.

3. A variable orifice pulse valve according to claim 2 wherein said variable orifice means and said sealing means are aligned along a line extending through said intermediate chamber.

4. A variable orifice pulse valve according to claim 1 further including a further chamber in fluid communication with said first opening of said valve.

5. A variable orifice pulse valve according to claim 1 further including an additional chamber in fluid communication with said second opening said valve.

6. A variable orifice pulse valve according to claim 1 wherein said first opening is in fluid communication with said inlet and said second opening is in fluid communication with said outlet for providing a pulsatile discharge of gas from said valve.

7. A variable orifice pulse valve according to claim 6 further including an inlet chamber between said inlet and said first opening of said intermediate chamber.

8. A variable orifice pulse valve according to claim 6 further including an outlet chamber between said second opening of said intermediate chamber and said outlet of said housing.

9. A variable orifice pulse valve according to claim 1 wherein the gas discharge from said valve is in the form of gas pulses having a desired quantity of gas, and wherein said intermediate chamber has a quantity less than the desired volume of the gas pulses.

10. A variable orifice pulse valve according to claim 9 wherein the volume of the said intermediate chamber is less than 50 $\mu$l.

11. A variable orifice pulse valve according to claim 10 wherein the volume of the said intermediate chamber is less than 20 $\mu$l.

12. A variable orifice pulse valve according to claim 11 wherein the volume of the said intermediate chamber is less than 10 $\mu$l.

13. A variable orifice pulse valve according to claim 12 wherein the volume of the said intermediate chamber is less than 5 $\mu$l.

14. A unitary, variable orifice pulse valve according to claim 1 further including means for urging said variable orifice forming means toward said first opening.

15. A variable orifice pulse valve according to claim 14 wherein said means for urging said variable orifice forming means toward said first opening comprises a solenoid responsive to an electrical signal.

16. A variable orifice pulse valve according to claim 1 wherein said first operating means comprises a solenoid responsive to an electric signal.

17. A variable orifice pulse valve according to claim 16, wherein said solenoid moves said variable orifice forming means away from said first opening by an amount determined in accordance with the magnitude of the electrical signal.

18. A variable orifice pulse valve according to claim 1 wherein said means for urging said sealing means into sealing engagement with said second opening comprises a spring.

19. A variable orifice pulse valve according to claim 1 wherein said means for urging said sealing means into sealing engagement with said second opening comprises a solenoid responsive to an electrical signal.

20. A variable orifice pulse valve according to claim 1 wherein said second operating means comprises a solenoid responsive to an electric signal.

21. A variable orifice pulse valve according to claim 1 wherein said housing has a further inlet for receiving a carrier gas for the gas discharged from said valve.

22. A variable orifice pulse valve according to claim 21 wherein said further inlet is in proximity to said outlet of said valve.

23. A variable orifice pulse valve according to claim 8 wherein said housing has a further inlet is connected to said outlet chamber to provide a carrier gas at a location and in a manner to sweep the discharged gas from said outlet chamber and prevent the discharged gas from being trapped in said outlet chamber.

24. A variable orifice pulse valve according to claim 23 wherein said further inlet is connected to said outlet chamber in proximity to said second opening of said intermediate chamber.

25. A variable orifice pulse valve according to claim 23 wherein said outlet chamber includes a portion extending along said sealing means and away from said second opening and wherein said further inlet is connected to said portion.

26. A variable orifice pulse valve according to claim 14 wherein said means for urging said variable orifice forming means toward said first opening comprises a spring.

27. A unitary, variable orifice pulse valve providing a discharge of gas in pulses having a preselected quantity of gas, said valve comprising:

a housing having an inlet for receiving gas and an outlet discharging gas from said valve;

a chamber formed in said chamber intermediate the inlet and outlet of said housing, said intermediate chamber having a first opening in fluid communication with said inlet and a second opening in fluid communication with said outlet, said intermediate chamber comprising a generally straight flow channel between said first and second openings having a volume less than the preselected quantity of gas in a gas pulse;

variable orifice forming means in said housing relatively movable with respect said first opening of said intermediate chamber;

means for urging said variable orifice forming means toward said first opening;

first operating means operatively associated with said variable orifice forming means, said first operating means moving said variable orifice forming means with respect to said first opening responsive to a variable magnitude signal applied to said first control means to cause said variable orifice forming means to form a variably sized orifice at said first opening for metering a quantity of gas, the size of said orifice being proportional to the magnitude of the signal;

sealing means in said housing relatively movable with respect to said second opening of said chamber for sealing and unsealing said second opening, said sealing means and said variable orifice means being aligned along a line extending through said intermediate chamber;

means for urging said sealing means into sealing engagement with said second opening to block fluid communication between said intermediate chamber and said outlet; and second operating means operatively associated with said sealing means, said second operating means being responsive to a signal applied thereto to move said second sealing means out of engagement with said second opening for a period of time to provide the pulsatile discharge of gas from said outlet of said valve.

28. A special gas dose delivery unit for respiration equipment, said respiration equipment supplying respiratory gases to a breathing circuit for provision to a patient, said special gas dose delivery unit providing a desired quantity of special gas in the breathing gases, the quantity of special gas being small compared to the volume of the breathing gases, said special gas dose delivery unit comprising:

a flow conduit (116) for the special gas, said flow conduit having one end connectable to a special gas source;

a special gas dosing conduit (112) having one end connectable to the breathing circuit;

a controllable valve (1) interposed between said flow conduit and said special gas dosing conduit, said valve being operable to provide doses of special gas into said special gas dosing conduit;

means (101) for setting desired parameters of the special gas doses; and a control unit (100), said control unit receiving an input from said parameter setting means, said control unit having an output connected to said controllable valve for operating said valve in accordance with said input for causing said valve to provide special gas doses into said special gas dosing conduit for delivery to the patient;

said controllable valve comprising a unitary, variable orifice pulse valve comprising:

a housing having an inlet coupled to said flow conduit for receiving special gas and an outlet coupled to said special gas dosing conduit;

a chamber formed in said housing intermediate the inlet and outlet of said housing, said chamber having a first opening in fluid communication with one of said inlet and outlet and a second opening in fluid communication with the other of said outlet and inlet;

variable orifice forming means in said housing relatively movable with respect said first opening of said chamber;

first operating means operatively associated with said variable orifice forming means, said first operating means moving said variable orifice forming means with respect to said first opening responsive to a variable magnitude signal applied to said first operating means to cause said variable orifice forming means to form a variably sized orifice at said first opening for metering a quantity of gas, the size of said orifice being proportional to the magnitude of the signal;

sealing means in said housing relatively movable with respect to said second opening of said chamber for sealing and unsealing said second opening;

means for urging said sealing means into sealing engagement with said second opening to block fluid communication through said second opening; and second operating means operatively associated with said sealing means, said second operating means being responsive to a signal applied thereto to move said sealing means out of engagement with said second opening for a period of time to provide a discharge of gas from said valve into said special gas dosing conduit for provision into the breathing gases of the patient as a dose of special gas.

29. A special gas dose delivery unit according to claim 28 further including means for urging said variable orifice forming means toward said first opening.

30. A special gas dose delivery unit according to claim 28 further including a carrier gas conduit, said housing having a further inlet coupled to said carrier gas conduit for receiving a carrier gas for the gas discharged from said valve.

31. A special gas dose delivery unit according to claim 30 wherein said further inlet is in proximity to said outlet of said valve.

32. Respiration equipment comprising:

a breathing circuit connectable to a patient for providing breathing gases to the patient;

a respirator supplying breathing gases to said breathing circuit; and a special gas dose delivery unit for providing a desired quantity of special gas in the breathing gases, the quantity of special gas being small compared to the volume of the breathing gases, said special dose delivery unit comprising:

a flow conduit (116) for the special gas, said flow conduit having one end connectable to a special gas source;

a special gas dosing conduit (112) having one end connected to the breathing circuit;

a controllable valve (1) interposed between said flow conduit and said special gas dosing conduit, said valve being operable to provide doses of special gas into said special gas dosing conduit;

means (101) for setting desired parameters of the special gas doses; and a control unit (100), said control unit receiving an input from said parameter setting means, said control unit having an output connected to said controllable valve for operating said valve in accordance with said input for causing said valve to provide special gas doses into said special gas dosing conduit for delivery to the patient;

said controllable valve comprising a unitary, variable orifice pulse valve comprising:

a housing having an inlet coupled to said flow conduit for receiving special gas and an outlet coupled to said special gas dosing conduit;

a chamber formed in said housing intermediate the inlet and outlet of said housing, said chamber having a first opening in fluid communication with one of said inlet and outlet and a second opening in fluid communication with the other of said outlet and inlet;

variable orifice forming means in said housing relatively movable with respect said first opening of said chamber;

first operating means operatively associated with said variable orifice forming means, said first operating means moving said variable orifice forming means with respect to said first opening responsive to a variable magnitude signal applied to said first operating means to cause said variable orifice forming means to form a variably sized orifice at said first opening for metering a quantity of gas, the size of said orifice being proportional to the magnitude of the signal;

sealing means in said housing relatively movable with respect to said second opening of said chamber for sealing and unsealing said second opening;

means for urging said sealing means into sealing engagement with said second opening to block fluid communication through said second opening; and second operating means operatively associated with said sealing means, said second operating means being responsive to a signal applied thereto to move said sealing means out of engagement with said second opening for a period of time to provide a discharge of gas from said valve into said special gas dosing conduit for provision into the breathing gases of the patient as a dose of special gas.

33. Respiration equipment according to claim 32 further including means for urging said variable orifice forming means toward said first opening.

34. Respiration equipment according to claim 32 further including a carrier gas conduit connected between said breathing circuit and a further inlet of said housing for supplying a carrier gas for the gas discharged from said valve.

35. Respiration equipment according to claim 34 wherein said further inlet is in proximity to said outlet of said valve.

* * * * *

UNITED STATES PATENT AND TRADEMARK OFFICE
CERTIFICATE OF CORRECTION

PATENT NO. : 6,032,667
DATED : March 7, 2000
INVENTOR(S) : Heinonen

It is certified that error appears in the above-indentified patent and that said Letters Patent is hereby corrected as shown below:

In the claims:

Claim 9, col. 7, line 60, delete "quantity" and substitute therefor --- volume--- ; Claim 9, col. 7, line 61, delete "volume" and substitute therefor --- quantity---

Signed and Sealed this

Tenth Day of April, 2001

Attest:

NICHOLAS P. GODICI

*Attesting Officer*    *Acting Director of the United States Patent and Trademark Office*